United States Patent
Irion et al.

(10) Patent No.: US 9,585,612 B2
(45) Date of Patent: Mar. 7, 2017

(54) MULTIFUNCTIONAL FLUORESCENCE DIAGNOSIS SYSTEM

(75) Inventors: Klaus M. Irion, Liptingen (DE); André Ehrhardt, Wurmlingen (DE); Reinhold Baumgartner, Freising (DE); Herbert Stepp, Planegg (DE); Thomas Pongratz, München (DE)

(73) Assignee: Karl Storz GmbH & Co. KG, Tuttlingen (DE)

( * ) Notice: Subject to any disclaimer, the term of this patent is extended or adjusted under 35 U.S.C. 154(b) by 303 days.

(21) Appl. No.: 11/361,484

(22) Filed: Feb. 24, 2006

(65) Prior Publication Data

US 2006/0241499 A1 Oct. 26, 2006

(30) Foreign Application Priority Data

Feb. 24, 2005 (DE) .................... 20 2005 003 411 U

(51) Int. Cl.
*A61B 6/00* (2006.01)
*G01N 21/64* (2006.01)
(Continued)

(52) U.S. Cl.
CPC .......... *A61B 5/413* (2013.01); *A61B 1/00009* (2013.01); *A61B 1/00186* (2013.01);
(Continued)

(58) Field of Classification Search
CPC ..... A61B 1/0638; A61B 1/444; A61B 1/0071; A61B 1/4416; A61B 5/413; A61B 5/00;
(Continued)

(56) References Cited

U.S. PATENT DOCUMENTS 4,600,302 A * 7/1986 Sage, Jr. .................... 356/39
6,200,310 B1 * 3/2001 Ben-Haim et al. ........... 606/10
(Continued)

FOREIGN PATENT DOCUMENTS

DE 694 33 413 T2 2/1995
WO WO 0150955 A1 * 7/2001

OTHER PUBLICATIONS

Weinberger, Andreas W.A. et al. Persistent indocyanine green (ICG) fluorescence 6 weeks after intraocular ICG administration for macular hole surgery. Graefe's Arch Clin Exp Opthalmol (2001) 239:388-390.*

(Continued)

*Primary Examiner* — Long V Le
*Assistant Examiner* — Helene Bor
(74) *Attorney, Agent, or Firm* — Whitmyer IP Group LLC

(57) ABSTRACT

A fluorescence diagnosis system has a viewing system at least one light source and a camera system. The at least one light source can be operated in three modes, a first generating white light, a second with a first fluorescence excitation light of a first excitation wavelength and a third in which a second fluorescence excitation light of a second excitation wavelength is generated producing a fluorescence image in the NIR range. The camera system is sensitive at least in the visible and the NIR range. The system further comprises an image processing system for converting the fluorescence image in the NIR range into a visible image.

22 Claims, 1 Drawing Sheet

(51) Int. Cl.
*A61B 5/00* (2006.01)
*A61B 1/00* (2006.01)
*A61B 1/04* (2006.01)
*A61B 1/06* (2006.01)
*A61B 1/307* (2006.01)

(52) U.S. Cl.
CPC ............ *A61B 1/043* (2013.01); *A61B 1/0638* (2013.01); *A61B 1/0646* (2013.01); *A61B 5/0071* (2013.01); *A61B 5/0084* (2013.01); *G01N 21/6428* (2013.01); *G01N 21/6456* (2013.01); *A61B 1/307* (2013.01); *A61B 5/721* (2013.01)

(58) Field of Classification Search
CPC ..... A61B 1/0646; A61B 1/06; A61B 1/00186; A61B 1/00; A61B 5/9984; A61B 1/00009; A61B 1/043; A61B 1/04; A61B 5/0071; A61B 1/307; A61B 1/721; G01N 21/6428; G01N 21/64; G01N 21/6456
USPC ...... 600/473, 476, 477, 310, 312; 250/494.1
See application file for complete search history.

(56) References Cited

U.S. PATENT DOCUMENTS

| | | | |
|---|---|---|---|
| 6,571,118 B1* | 5/2003 | Utzinger et al. | 600/476 |
| 6,574,502 B2* | 6/2003 | Hayashi | 600/476 |
| 6,790,174 B2* | 9/2004 | Kaneko et al. | 600/118 |
| 6,821,245 B2* | 11/2004 | Cline et al. | 600/160 |
| 6,912,412 B2* | 6/2005 | Georgakoudi et al. | 600/310 |
| 6,936,004 B2* | 8/2005 | Utsui | 600/182 |
| 6,960,165 B2* | 11/2005 | Ueno et al. | 600/181 |
| 6,962,565 B2* | 11/2005 | Nakamura | 600/179 |
| 7,043,291 B2* | 5/2006 | Sendai | 600/478 |
| 7,062,311 B1* | 6/2006 | Sendai et al. | 600/407 |
| 7,103,402 B2* | 9/2006 | Vo-Dinh | 600/476 |
| 2002/0065468 A1* | 5/2002 | Utzinger et al. | 600/476 |
| 2002/0072677 A1* | 6/2002 | Sevick-Muraca et al. | 600/473 |
| 2002/0138008 A1* | 9/2002 | Tsujita et al. | 600/473 |
| 2003/0130579 A1* | 7/2003 | McClane et al. | 600/476 |
| 2003/0229270 A1* | 12/2003 | Suzuki et al. | 600/178 |
| 2004/0006276 A1* | 1/2004 | Demos et al. | 600/476 |
| 2004/0162489 A1* | 8/2004 | Richards-Kortum et al. | 600/473 |
| 2004/0186383 A1* | 9/2004 | Rava et al. | 600/473 |
| 2004/0199079 A1* | 10/2004 | Chuck et al. | 600/477 |
| 2004/0215060 A1* | 10/2004 | Ueno et al. | 600/160 |
| 2004/0225222 A1* | 11/2004 | Zeng et al. | 600/476 |
| 2005/0059894 A1* | 3/2005 | Zeng et al. | 600/476 |
| 2005/0065406 A1* | 3/2005 | Cline et al. | 600/160 |
| 2005/0085732 A1* | 4/2005 | Sevick-Muraca et al. | 600/473 |
| 2005/0143663 A1* | 6/2005 | Liu et al. | 600/476 |
| 2005/0240107 A1* | 10/2005 | Alfano et al. | 600/476 |
| 2005/0261592 A1* | 11/2005 | Suga | 600/478 |
| 2005/0288556 A1* | 12/2005 | Sugimoto | 600/160 |
| 2006/0089554 A1* | 4/2006 | Ishihara et al. | 600/476 |
| 2006/0149133 A1* | 7/2006 | Sugimoto et al. | 600/160 |
| 2006/0155193 A1* | 7/2006 | Leonardi et al. | 600/473 |

OTHER PUBLICATIONS

Izzetoglu, M.; Izzetoglu, K.; Bunce, S.; Ayaz, H.; Devaraj, A.; Onaral, B.; Pourrezaei, K., "Functional near-infrared neuroimaging," Neural Systems and Rehabilitation Engineering, IEEE Transactions on [see also IEEE Trans. on Rehabilitation Engineering], vol. 13, No. 2, pp. 153-159, Jun. 2005 URL: http://ieeexplore.ieee.org/iel5/7333/31004/0143953.*

Endo World URO Nr. 17/5-D, 2000 pp. 1 to 12 and English Equivalent of 1998.

* cited by examiner

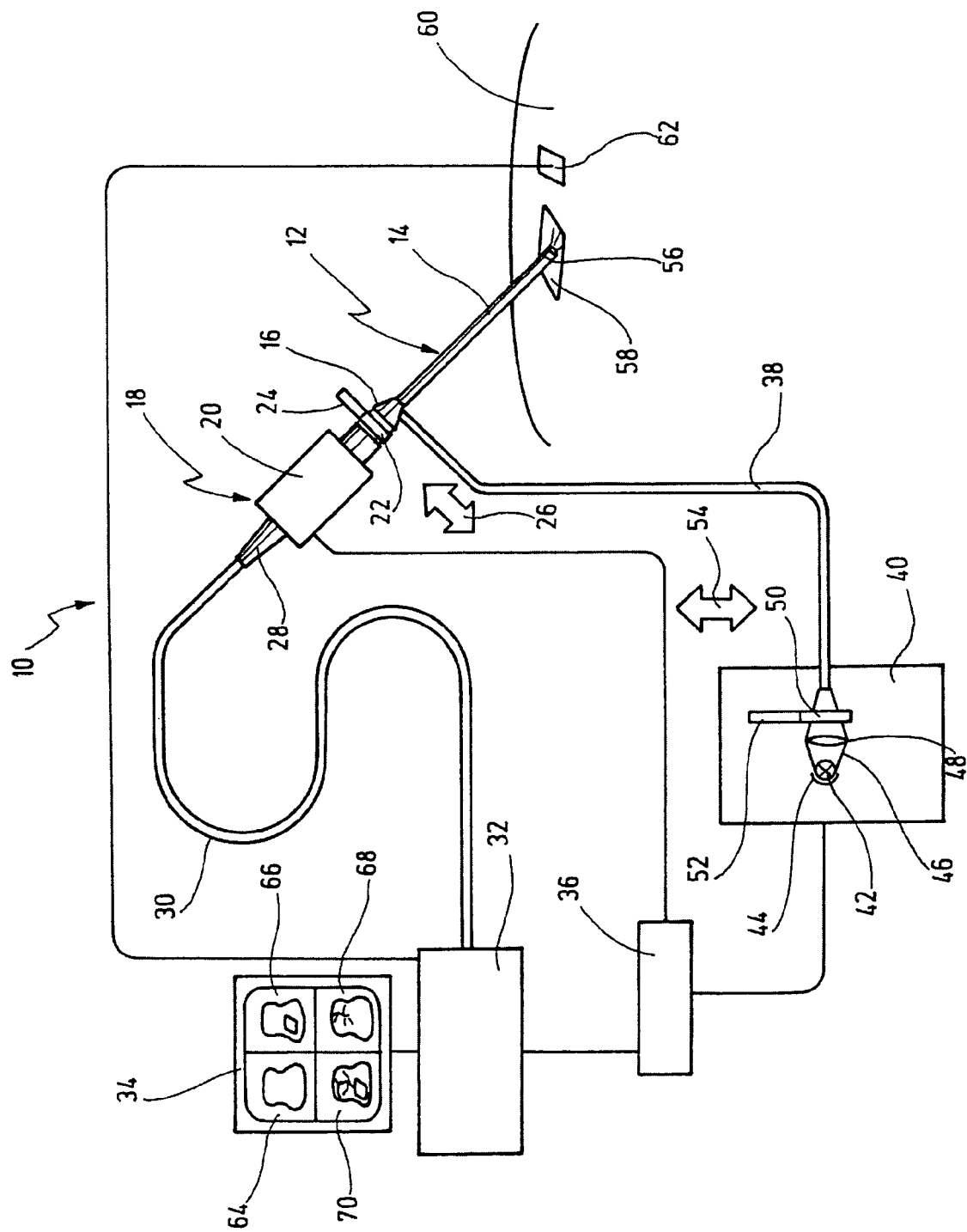

MULTIFUNCTIONAL FLUORESCENCE DIAGNOSIS SYSTEM

CROSS-REFERENCE TO RELATED APPLICATIONS

This application claims priority of German patent application No. DE 20 2005 003 411.8 filed on Dec. 24, 2005.

BACKGROUND OF THE INVENTION

The present invention relates to a fluorescence diagnosis system.

Such a fluorescence diagnosis system is used, for example, for what is called photodynamic diagnosis of tumors. In photodynamic diagnosis, a patient is administered a suitable tumor marker substance, for example 5-aminolevulinic acid (5-ALA). 5-ALA is a precursor in heme biosynthesis. 5-ALA collects in tumor tissue and causes a fluorescence that can be excited with a specific wavelength. Areas in which 5-ALA has collected, that is to say tumorous areas, fluoresce in a red color. Since blue light is used as the excitation light, this can be filtered out in the observed view, and the tumorous areas thus stand out clearly from the healthy tissue.

It is also known that healthy tissue fluoresces at certain wavelengths of the excitation light even without addition of a marker. This phenomenon is referred to as autofluorescence. Tumor tissue, by contrast, hardly fluoresces at all. It appears dark in contrast to the surrounding healthy tissue and can in this way be distinguished from the healthy tissue.

This phenomenon too can be used to distinguish fluorescing tumor cells from surrounding healthy tissue. This autofluorescence, however, is generally much weaker than the fluorescence generated by a tumor marker, so that this form of diagnosis has a somewhat less important role.

Systems for photodynamic diagnosis, for example for early detection of bladder carcinoma, are marketed by the Applicant and are described, inter alia, in Endo World URO No. 17/5-D, 2000, pages 1 through 12. The main feature of this system is the D-LIGHT light system which is able to generate both white light and also fluorescence excitation light.

Usually such a system comprises the following: a viewing system, at least one light source, and a camera system for recording an image taken by the viewing system, the at least one light source being able to be operated in a first operating mode in which white light is generated, leading to a white light image, and the at least one light source being able to be operated in a second operating mode in which a first fluorescence excitation light of a first excitation wavelength range is generated, producing a fluorescence image in the visible range.

Endoscopic systems are used as the viewing system. However, it is also conceivable to use other viewing systems such as microscopic systems. It is furthermore possible for the viewing system and the camera system to be combined in one unit, for example in the form of a video endoscope.

Using such a system, the morphological structure of the surface of a hollow organ can be imaged and, with the aid of suitable tumor markers or the aforementioned autofluorescence, tumors can be distinguished with great contrast from normal tissue.

However, it is not possible to present certain functional properties of the tissue with this system. Among these functional properties, particular mention may be made of the perfusion of blood vessels.

The ability to view the perfusion would provide an operating surgeon with a further aid to distinguishing tumor tissue from surrounding healthy tissue. In addition, by the ability to view these functional properties of the tissue, the possible applications of such a system could be greatly extended, for example to check the status of tissue after transplantation, for example.

Methods for viewing the circulation of blood through a tissue are known per se. Thus, DE 694 33 413 T2 discloses a method in which a dye is injected into a patient's eye in order to view choroidal neovascularization, said dye filling the vascular structures of the eye. This dye can then be excited to fluorescence with the aid of excitation light in the range of the absorption maximum of the dye.

A dye used in this method and in related methods is indocyanine green (ICG). This dye has the structural formula shown below and has its absorption maximum at a wavelength of ca. 800 nm.

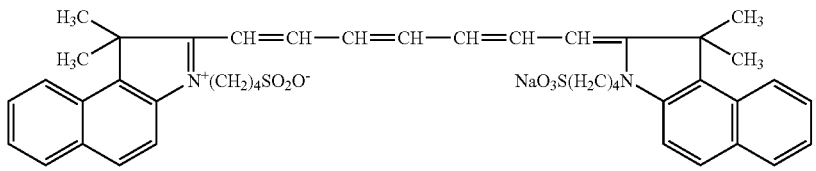

indocyanine green

When ICG is excited to fluorescence by excitation light, it has a fluorescence maximum at ca. 840 nm. Both the absorption maximum and also the fluorescence maximum of ICG lie in the so-called near infrared range (NIR range). Since human tissue is relatively transparent in the NIR range, radiation in the NIR range can pass quite far through the tissue, and deeper-lying vessel structures can be made visible.

ICG also has the property of binding to proteins present in the blood plasma and, after its administration, does not pass out of the blood vessels and into the surrounding tissue to any great extent.

The object of the present invention is to make available a system with which it is possible to gather various kinds of information concerning the site that is to be viewed.

SUMMARY OF THE INVENTION

According to the invention, the object is achieved by the fact that the at least one light source can be operated in a third operating mode in which a second fluorescence excitation light of a second excitation wavelength range is generated, producing a fluorescence image in the NIR range, and the camera system is sensitive at least in the visible and in the NIR range, and the fluorescence diagnosis system further comprises an image processing system with which the fluorescence image in the NIR range can be converted into a visible image.

By providing a third operating mode for the at least one light source, it is possible, in addition to the known excitation of fluorescence of a tumor marker or autofluorescence, also to excite the fluorescence of a dye which, after its administration, distributes itself in a specific manner in the blood vessels.

The use of excitation light in the NIR range has the advantage that it is absorbed only weakly by human tissue, with the result that deeper-lying blood vessels can also be viewed. In addition, the excitation frequency range in the NIR range differs greatly from that of the most commonly used tumor marker 5-ALA, whose excitation frequency range lies in the blue wavelength range.

By using an image processing system, it is also made possible to render visible the NIR range fluorescence which is not visible to the human eye. This can be done in different colors, for example if the fluorescence signal in the NIR range is intended to be superposed with other signals. The fluorescence signal can, for example, be presented in a green color, since this provides a particularly high contrast to the reddish tones normally occurring in the human body. When using 5-ALA as the tumor marker, the tumor tissue also fluoresces in red. Thus, presentation of the fluorescence signal in a green color provides a good contrast in this case, even with superposition of the images of the second and third operating modes.

As has been described above, in the use of autofluorescence, the tumor tissue appears dark. Here, presentation of the fluorescence signal in the NIR range, for example in a red color, is suitable for achieving sufficient contrast. The color in which the fluorescence signal is presented can advantageously be determined as a function of the other signals presented.

Thus, a multifunctional fluorescence diagnosis system is made available in which, with a single unit, three different images can be recorded of an area of the human body that is to be examined. Thus, with just a single instrument, a large amount of information can be made available to an operating surgeon in a simple and compressed form.

In one embodiment of the present invention, images or image sequences recorded by the camera system can be stored with the image processing system.

This embodiment has the advantage that, after the actual examination, it allows the operating surgeon to again look at the images taken during the examination, thus facilitating a more accurate analysis of the images.

The recording of image sequences is useful particularly in the recording of time-dependent profiles. This includes, for example, the distribution of a dye such as ICG in blood vessels, when this is introduced into the blood vessels.

In a further embodiment of the invention, an image sequence can be stored automatically with the image processing system when the at least one light source is switched to the third operating mode.

The distribution of a dye in blood vessels is in particular a time-dependent and often very rapid process, since the dye does not remain in the blood vessels but simply flows through them. Further information on the blood vessels can be obtained from the flow characteristics over a given period of time.

By means of the abovementioned measure, it is now ensured that an image sequence is automatically recorded when switching to the third operating mode, with the result that an operating surgeon does not have to give consideration to triggering the recording of an image sequence himself.

In a further embodiment of the invention, storage of an image sequence can be automatically switched off with the image processing system when the at least one light source is switched from the third operating mode to the first or second operating mode.

This measure further facilitates the work of the operating surgeon since, when switching from the third operating mode to another operating mode of the at least one light source, he does not additionally have to interrupt the recording of an image sequence.

In a further embodiment of the invention, the image processing system can be configured such that storage of the image sequence can be automatically switched off in the third operating mode of the at least one light source when a fluorescence signal drops below a predeterminable value.

This means that the storage of the image sequence is automatically terminated when most of the dye has been flushed out of the blood vessels. By combination with the abovementioned measure, the recording of the flow characteristics of the dye in the blood vessels can thus be fully automated, which further facilitates the work of the operating surgeon.

In a further embodiment of the invention, the fluorescence diagnosis system further comprises at least one sensor which measures the concentration of a dye.

Such a sensor can fulfill various duties. Thus, for example, it is possible, after administration of the dye, to detect the latter's presence and then automatically trigger a switch to the third operating mode of the light source. This further facilitates the work of the operating surgeon.

It is also known that, after high-pressure injection of a dye, a bolus with a relatively sharply defined leading edge forms. With the aid of the abovementioned sensor and with either the fluorescence diagnosis system itself or a further sensor, it is possible to measure the speed with which the bolus moves through a blood vessel. Further information on the examined area can thus be made available to an operating surgeon.

In a further embodiment of the invention, two or more images or image sequences from individual operating modes of the at least one light source can be processed with the image processing system to form one image or one image sequence.

This embodiment allows different image data to be superposed with one another during an examination, for example intermittently, or after completion of an examination. Thus, for each desired point in time during the examination, the operating surgeon is able to select an individual combination of the image data presented to him. This combination of possible views thus increases the information available to the operating surgeon.

In a further embodiment of the invention, the fluorescence diagnosis comprises a connection between the at least one light source and the camera system.

This embodiment has the advantage that, by means of the connection to the light source, the camera system is always automatically set in an ideal manner to the operating mode used by the light source. This can be achieved, for example, by the use of filters in or on the camera system, said filters filtering out the fluorescence excitation light which is used by the light source and which could otherwise possibly overlap the fluorescence that is to be viewed. Thus, the best possible fluorescence signal can always be recorded by the camera system.

In a further embodiment of the invention, the at least one light source is an incoherent light source.

An incoherent light source has the advantage that a broad-band spectrum can inexpensively be generated which provides desired excitation light through the introduction of suitable filters.

In a further embodiment of the invention, in the third operating mode of the at least one light source, light can be emitted at wavelengths lying in the excitation wavelength range of ICG.

As has already been mentioned above, ICG is a particularly suitable dye for viewing blood vessels. Since blood vessels are particularly important for the analysis of functional properties of a tissue, ICG is particularly preferably used. In order to view ICG as efficiently as possible, the wavelength of the light in the third operating mode is matched to the excitation wavelength range of ICG.

In a further embodiment of the invention, the at least one light source in the third operating mode has a filter which transmits light in the wavelength range of 650 to 770 nm and which blocks light in the wavelength range starting from 780 nm.

This embodiment and the following embodiment in turn ensure that the fluorescence diagnosis system in the third operating mode is optimized to the use of ICG as dye.

Although ICG exhibits its absorption maximum at approximately 800 nm, it can already be excited to fluorescence at a wavelength of ca. 650 nm. Since the fluorescence maximum of ICG at 840 nm lies near the absorption maximum of 800 nm, an excitation light with a wavelength of 800 nm would already overlap a considerable part of the fluorescence signal of ICG. This fluorescence signal drops sharply in the direction of the shorter wavelength and is minimal at about 760 nm. By limiting the fluorescence excitation light to a wavelength of at most 780 nm, it is thus possible to obtain a particularly advantageous balance between maximum fluorescence excitation and minimal overlap of the fluorescence signal.

In a further embodiment of the invention, the viewing system has, in the third operating mode of the at least one light source, a filter which transmits light in the wavelength range of 800 to 900 nm and which blocks light at least in the wavelength range of 380 to 790 nm.

This filter blocks the light which has a shorter wavelength than the fluorescence light and can therefore no longer overlap the fluorescence signal of the ICG in the recording of the image. Particularly efficient recording of the fluorescence signal of the ICG is thus achieved.

In a further embodiment of the invention, the fluorescence diagnosis system further comprises a sensor for detecting an ECG signal. In particular, image data can be stored in synchrony with the ECG signal in the third operating mode of the at least one light source.

The speed of flow of the blood in blood vessels is influenced by the patient's pulse. As a result, especially in examinations of the heart and also of major vessels, the flow of a dye through the blood vessels can be subject to deviations and so-called movement artefacts.

If the fluorescence diagnosis system now has a sensor for recording an ECG signal, this signal can be used to trigger the storage of image data. This technique is also referred to as ECG triggering. By this means, the image data are recorded in phase synchronization, that is to say the image data are always recorded at the same point during a heart beat, for example in synchronization with the QRS complex or the R wave. In this way, such artefacts can be avoided.

It will be appreciated that the aforementioned features and those still to be mentioned below can be used not only in the respectively cited combination, but also in other combinations or singly, without departing from the scope of the present invention.

BRIEF DESCRIPTION OF THE DRAWINGS

FIG. 1 shows a schematic construction of a fluorescence diagnosis system

DETAILED DESCRIPTION OF A PREFERRED EMBODIMENT

In FIG. 1, a fluorescence diagnosis system is designated in its entirety by reference number 10.

The fluorescence diagnosis system 10 comprises a viewing system 12, which is here designed as an endoscope 14. The design of the viewing system 12 as an endoscope 14 is preferred, since tissue inside a patient's body can in this way be examined while causing the patient minimal stress. However, other viewing systems are also conceivable, for example microscopes. At a proximal end 16, the endoscope 14 has a camera system 18, which is here designed as a video camera 20. The camera system 18 and the endoscopes 14 can also be designed in one unit, for example in the form of a video endoscope. A filter 22 is also arranged between the video camera 20 and the proximal end 16 of the endoscope 14.

The filter 22 is connected to a further filter 24 and can be moved, in the direction of a double arrow 26, between the video camera 20 and the proximal end 16 of the endoscope 14. By moving the filters 22, 24 in the direction of the double arrow 26, it is possible either to switch to and fro between the two filters 22, 24, or the filters 22 and 24 can be removed completely from between the video camera 20 and the proximal end 16 of the endoscope 14.

The filters 22, 24 are used to set the video camera 20 optimally to the operating mode of the fluorescence diagnosis system 10. Thus, for example, the filter 22 can filter out excitation light in the frequency range of 800 nm or less that is used for excitation of ICG, while the filter 24 can be used to filter out excitation light used for excitation of 5-ALA.

When using 5-ALA, the fluorescence excitation takes place in the blue wavelength range, at approximately 380 to 430 nm. The fluorescence takes place at a wavelength of about 635 nm. The filter 24 is therefore designed to block light with a wavelength of less than 550 nm and to transmit light with a greater wavelength. If the aim is to generate a white light image of a tissue that is to be examined, the filters 22, 24 can be completely removed.

At the proximal end, the video camera 20 has a plug 28 via which the video camera 20 is connected by a cable 30 to an image processing system 32.

This image processing system 32 is used both to process and also to store image data recorded by the video camera 20, such as images or image sequences. The image processing system 32 further comprises a display screen 34 on which the image data recorded by the video camera 20 can be displayed.

The video camera 20 is moreover connected to a camera control unit 36 which is likewise connected to the image processing system 32 and serves to control different functions of the video camera 20, for example in feedback, with the image processing system 32.

The endoscope 14 is also connected to a light source 40 via a light guide 38. This light source 40 is likewise connected to the camera control unit 36 such that the video camera 20 can be set optimally to the different operating modes of the light source 40 with the camera control unit 36.

The light source 40 comprises a xenon lamp 42 which is partially surrounded by a reflector 44. The xenon lamp 42 serves to generate light with the widest possible wavelength range. The light generated by the xenon lamp 42 and reflected by the reflector 44 forms a light beam 46 which is directed to a positive lens 48. This positive lens 48 bundles the light beam 46 and leads it through a filter 50.

The filter 50 is connected to a second filter 52, the filters 50, 52 being able to be moved in the direction of a double arrow 54.

By moving the filters 50, 52 in the direction of the double arrow 54, the filter 50 or the filter 52 can in each case be brought into the light beam 46. Moreover, both filters 50, 52 can be removed from the light beam. In this way, the various operating modes of the light source 40 are established.

The filter 50 is designed to transmit only light in the wavelength range of 650 to 770 nm and to block light in a wavelength range of over 780 nm. In this way, only fluorescence excitation light for ICG leaves the filter 50, while at the same time the wavelength range in which ICG generates a fluorescence signal is filtered out, such that this does not superpose the fluorescence signal of the ICG. This corresponds to the third operating mode of the light source 40.

Correspondingly, the filter 52 is designed to transmit light with a wavelength in the range of 380 to 430 nm (excitation range when using 5-ALA) and to block light with a wavelength range of more than 450 nm. In this way, effective excitation of the fluorescence is achieved without the irradiated excitation light overlapping the fluorescence signal. The positioning of the filter 52 in the light beam 46 corresponds to the second operating mode of the light source 40.

If the aim is to obtain a white light image of the tissue that is to be examined, the filters 50, 52 can be removed completely from the light beam 46. This position corresponds to the first operating mode of the light source 40.

If appropriate after passing through the filters 50, 52, the light beam 46 is coupled into the light guide 38 and conveyed to a distal end 56 of the endoscope 14. This distal end 56 of the endoscope 14 can, for example, be introduced through an incision 58 into a body 60 of a patient, in order to examine tissue located there. If appropriate, in order to examine the tissue, the patient is also administered the desired fluorescence dyes, such as ICG or 5-ALA. It is thus possible, via just a small incision, and thereby causing the patient less stress, to diagnose the presence of tumor tissue for example.

The fluorescence diagnosis system further comprises ECG sensors, of which only the sensor 62 is shown here for the sake of simplicity. This sensor 62 is in turn connected to the image processing system 32, and the signal recorded by the sensor 62 is stored by the image processing system 32 and made available for further processing.

The image processing system 32 is also configured such that the signal of the sensor 62 can be used to control the storage of an image or image sequence recorded by the video camera, for example by triggering to the QRS complex of the ECG signal. Thus, for example, one image can be recorded in phase synchronization per heart beat. In this way, when viewing vascular systems, it is possible to avoid movement artefacts caused by the patient's pulse. Moreover, if one image is recorded in phase synchronization per heart beat, it is possible to achieve phase integration in order to obtain further information.

An examination using the fluorescence diagnosis system 10 is performed as follows:

The light source 40 is set in the first operating mode and generates white light. The endoscope 14 can now be introduced, with visual monitoring, through the incision 58 into the body 60 of a patient. The video camera 20 delivers a white light image of the tissue that is to be examined, which image is presented in a first quadrant 64 of the display screen 34.

This white light image can be used for a first visual examination of the tissue or also for guiding further instruments to the site of the tissue that is to be examined.

If the examination is being performed for the purpose of diagnosing tumors, the patient is first administered 5-ALA. If a tumor is situated in the area of the tissue that is to be examined, 5-ALA accumulates therein and is converted to photoporphyrin XI. This accumulation and conversion takes place mainly in tumor cells. Photoporphyrin XI can be excited to fluorescence in the wavelength range of 380 to 430 nm and fluoresces in the range of 635 nm. The tumors in which 5-ALA has accumulated thus fluoresce in a red color.

If the light source 40 of the diagnosis system 10 is set into the second operating mode, it generates fluorescence excitation light in the range of 380 to 430 nm. This excites fluorescence in the marked tumor. The fluorescing tumors are thus made visible and are presented in a second quadrant 66 of the display screen 34.

To permit visualization of blood vessels, an ICG solution is injected into the tissue to be examined, and the light source 40 is switched to the third operating mode. The ICG flows through the blood vessels present in the tissue to be examined and is excited to fluorescence by the fluorescence excitation light generated by the light source 40.

The video camera 20 picks up the fluorescence signal of the ICG, and this signal is presented in a third quadrant 68 of the display screen 34. A malignant tumor is often characterized by particularly strong vascularization.

The three images from the three operating modes are collated by the image processing system 32 and are presented as one image in a fourth quadrant 70 of the display screen 34. The signals from the second and third operating modes of the light source 40 are advantageously presented in colors which contrast with the red tones present in the body, for example in green or in blue.

From the view presented in the fourth quadrant 70 of the display screen 34, the operating surgeon can quickly ascertain whether tumors are present and, if so, where they are located and how strongly they are vascularized. From the vascularization, it is possible in turn to draw conclusions as to whether malignant tumors are present.

What is claimed is:

1. A method for analyzing an area of tissue, comprising:
   illuminating the area of tissue to be analyzed using white light;
   producing a first image of the area of tissue based on the white light, wherein the white light contains all the wavelengths of visible light;
   illuminating the area of tissue using a first fluorescence excitation light of a first excitation wavelength range;
   producing a second image of the area of tissue using fluorescence excited by the first fluorescence excitation light;
   introducing a dye that is excitable to fluoresce in a near-infrared range by an excitation light of a second excitation wavelength range into the area of tissue;

illuminating the area of tissue using a second fluorescence excitation light of the second excitation wavelength range selected to excite fluorescence of the dye;

producing a third image of the area of tissue using fluorescence excited by the second fluorescence excitation light in response to detection of the dye by a sensor;

upon production of the third image, storing the third image, both automatically and in phase synchrony with an ECG signal in an image processing system;

converting the third image in the near-infrared range to a fourth image in a visible range; and displaying the first, second, and third or fourth images simultaneously to a user.

2. The method of claim 1, wherein said step of producing the third image further comprises producing a third image sequence;

wherein said step of converting the third image further comprises converting the third image sequence in the near-infrared range to a fourth image sequence in a visible range; and wherein said step of storing further comprises storing at least one of the third and fourth image sequences in the image processing system.

3. The method of claim 1, further comprising:

sensing the strength of the fluorescence excited by the second fluorescence excitation light; and ceasing said storing automatically when the strength of the fluorescence excited by the second fluorescence excitation light drops below a predetermined value.

4. The method of claim 1, wherein said step of illuminating the area of tissue using a second fluorescence excitation light further comprises filtering all portions of the spectrum of white light except for the range of about 650 nm to 770 nm.

5. The method of claim 1, wherein said step of producing a third image further comprises filtering all portions of the spectrum of a received signal below about 800 nm.

6. The method of claim 1, further comprising the step of processing the first, second, and third or fourth images into a collated image; and wherein the step of displaying further comprises displaying the collated image simultaneously with the first, second, and third or fourth images.

7. The method of claim 1, wherein the steps of producing the first and second images further comprise producing respective first and second image sequences; and wherein the method further comprises the step of processing the first, second, and third or fourth image sequences into a collated image sequence.

8. The method of claim 1, wherein the step of introducing a dye further comprises introducing indocyanine green (ICG).

9. A fluorescence diagnosis system, comprising a viewing system;

at least one light source, comprising a first operating mode in which white light is generated, producing a white light image, wherein the white light contains all the wavelengths of visible light, a second operating mode in which a first fluorescence excitation light of a first excitation wavelength range is generated, producing a fluorescence image in a visible range, and a third operating mode in which a second fluorescence excitation light of a second excitation wavelength range is generated, producing a fluorescence image in a near-infrared range;

a camera system sensitive in at least the visible range and the near-infrared range for recording an image taken by said viewing system;

at least one sensor that detects the presence of a dye that is excitable to fluoresce in the near-infrared range and adapted to automatically switch said at least one light source into the third operating mode upon detection of the dye;

a sensor for detecting an ECG signal;

an image processing system adapted to convert the fluorescence image in the near-infrared range into a visible image and adapted to automatically store images produced by said camera system when said at least one light source is switched into the third operating mode, wherein storing of images produced by said camera system is in phase synchrony with the ECG signal provided by the sensor for detecting the ECG signal; and a display adapted to simultaneously display the white light image, the fluorescence image in a visible range, and the fluorescence image in the near-infrared range as separate images on the viewing system.

10. The fluorescence diagnosis system of claim 9, wherein an image sequence recorded by said camera system can be stored within said image processing system.

11. The fluorescence diagnosis system of claim 10, wherein said image processing system is adapted to automatically switch off storage of said image sequence when said at least one light source is switched from said third operating mode to said first or second operating mode.

12. The fluorescence diagnosis system claim 10, wherein said image processing system is adapted to automatically switch off storage of said image sequence in said third operating mode of said at least one light source when a fluorescence signal drops below a predeterminable value.

13. The fluorescence diagnosis system of claim 9, wherein said image processing system is adapted to process at least two images from individual operating modes of said at least one light source to form a single image.

14. The fluorescence diagnosis system of claim 9, wherein said image processing system is adapted to process at least one image sequence from individual operating modes of said at least one light source to form at least one collated image sequence.

15. The fluorescence diagnosis system of claim 9, wherein said system further comprises a connection between said at least light source and said camera system.

16. The fluorescence diagnosis system of claim 9, wherein said at least one light source is an incoherent light source.

17. The fluorescence diagnosis system of claim 9, wherein in said third operating mode of said at least one light source, light is emitted at wavelengths lying in an excitation wavelength range of indocyanine green (ICG).

18. The fluorescence diagnosis system of claim 9, wherein said at least one light source in said third operating mode uses a filter which only transmits lights in a wavelength range of about 650 nm to about 770 nm.

19. The fluorescence diagnosis system of claim 9, wherein said viewing system uses, in said third operating mode of said at least one light source, a filter that only transmits light in a wavelength range of above about 800 nm.

20. The fluorescence diagnosis system of claim 9, wherein said image processing system is adapted to form a collated image by collating the white light image, the fluorescence image in a visible range, and the fluorescence image in a near-infrared range.

21. The fluorescence diagnosis system of claim 20, wherein the image processing system is adapted to simultaneously display the collated image, the white light image, the fluorescence image in a visible range, and the fluorescence image in a near-infrared range as separate images on the viewing system.

22. A method for analyzing an area of tissue, comprising the following steps in the following order:
- illuminating the area of tissue to be analyzed using white light;
- producing a first image of the area of tissue based on the white light, wherein the white light contains all the wavelengths of visible light;
- illuminating the area of tissue using a first fluorescence excitation light of a first excitation wavelength range;
- producing a second image of the area of tissue using fluorescence excited by the first fluorescence excitation light;
- introducing a dye that is excitable to fluoresce in a near-infrared range by an excitation light of a second excitation wavelength range into the area of tissue;
- illuminating the area of tissue using a second fluorescence excitation light of the second excitation wavelength range selected to excite fluorescence of the dye;
- producing a third image of the area of tissue using fluorescence excited by the second fluorescence excitation light in response to detection of the dye by a sensor;
- upon production of the third image, storing the third image, both automatically and in phase synchrony with an ECG signal in an image processing system;
- converting the third image in the near-infrared range to a fourth image in a visible range; and
- displaying the first, second, and third or fourth images simultaneously to a user.

* * * * *